United States Patent
Mathis

(10) Patent No.: US 6,190,736 B1
(45) Date of Patent: Feb. 20, 2001

(54) PROCESS FOR PROVIDING FIBRES OR NONWOVENS WITH A HYDROPHILIC COATING

(75) Inventor: Raymond Mathis, Duesseldorf (DE)

(73) Assignee: Henkel Kommanditgesellschaft auf Aktien, Duesseldorf (DE)

( * ) Notice: Under 35 U.S.C. 154(b), the term of this patent shall be extended for 0 days.

(21) Appl. No.: 09/230,300

(22) PCT Filed: Jul. 15, 1997

(86) PCT No.: PCT/EP97/03783

§ 371 Date: Jul. 26, 1999

§ 102(e) Date: Jul. 26, 1999

(87) PCT Pub. No.: WO98/03716

PCT Pub. Date: Jan. 29, 1998

(30) Foreign Application Priority Data

Jul. 23, 1996 (DE) .............................. 196 29 667

(51) Int. Cl.⁷ ................. B05D 1/36; B05D 3/02
(52) U.S. Cl. ............... 427/384; 427/394; 427/402
(58) Field of Search ....................... 427/384, 394, 427/396, 402

(56) References Cited

U.S. PATENT DOCUMENTS 5,035,814  7/1991  Maaser ................. 252/8.7
5,045,387  9/1991  Schmalz ............... 428/284

FOREIGN PATENT DOCUMENTS

| 33 09 530 | 10/1984 | (DE) . |
| 37 02 286 | 8/1987 | (DE) . |
| 0 372 890 | 6/1990 | (EP) . |
| 0 395 099 | 10/1990 | (EP) . |
| 57-205513 | * 12/1982 | (JP) . |
| 2-084543 | * 3/1990 | (JP) . |
| 7-268773 | * 10/1995 | (JP) . |

OTHER PUBLICATIONS

Ullmann's Encyclopedia of Industrial Chemistry, Fifth Edition (revised), vol. A17, VCH Weinheim, 1994, pp. 572–583.

"Durable Hydrophilic Finishes For Olefinic Nonwovens, Films (Including Apertured) and Laminates in Disposable Articles", Research Disclosure No. 353, Sep., 1993, p. 593.

* cited by examiner

Primary Examiner—Erma Cameron
(74) Attorney, Agent, or Firm—John E. Drach; Steven J. Trzaska

(57) ABSTRACT

A process for hydrophilically finishing synthetic fibers or nonwoven substrates containing synthetic fibers involving applying an effective amount of a finish composition onto the fibers or nonwoven substrates, the finish composition containing from 75 to 100% by weight, based on the weight of the composition, of at least one monoester of glycerol and a fatty acid having from 6 to 14 carbon atoms.

20 Claims, No Drawings

PROCESS FOR PROVIDING FIBRES OR NONWOVENS WITH A HYDROPHILIC COATING

BACKGROUND OF THE INVENTION

This invention relates to a process for the hydrophilic finishing of fibers, which exclusively or predominantly contain polyolefins or polyesters, or of nonwovens containing polyolefin or polyester fibers and to fibers or nonwovens which are given a hydrophilic finish by this process.

In the manufacture of sanitary articles, such as diapers or sanitary napkins, absorbent materials are used to absorb aqueous liquids. In order to prevent direct contact with the absorbent material during wear and to increase comfort, the absorbent material is wrapped in a thin water-permeable nonwoven. The nonwovens used for this purpose are normally made of synthetic fibers, such as polyolefin or polyester fibers, because fibers such as these are inexpensive to produce, exhibit good mechanical properties and, in the case of polyolefin, can be thermobonded. However, untreated polyolefin or polyester fibers are not suitable for this particular application because, in view of their hydrophobic surface, they are not sufficiently permeable to aqueous liquids. Accordingly, the fiber surface has to be made hydrophilic by a corresponding finish. It is also desirable that the hydrophilic finish of the fibers should remain intact for as long as possible without any reduction in the permeability to water of the nonwoven. If nonwovens of the type in question are made up, for example, into diapers, the diapers thus produced can be subjected to repeated stressing without becoming leaky. In this way, the wearing time of the diapers is increased and the waste caused by used diapers can be reduced accordingly.

U.S. Pat. No. 5,045,387 describes, for example, a formulation for the hydrophilic finishing of polyolefin fibers which contains a mixture of an alkoxylated ricinoleic acid derivative, a hydrogenated ricinoleic acid derivative, a $C_{18}$ fatty acid and a polyalkoxylated polymethyl siloxane. EP 372 890 B1 discloses fibers which contain polyolefins or polyesters and which have been treated with a finish containing a fatty acid diethanolamide, a polyether-modified silicone, a sorbitan fatty acid ester and a metal salt of an alkyl sulfonate. The disadvantage of finishes such as these lies above all in their high price. In addition, correspondingly finished fibers show poorer behavior in the nonwoven production process, particularly during thermobonding, which results in reduced strength of the nonwoven. EP 395 099 A2 describes absorbent materials, more especially tampons of rayon or polyester fibers, which are finished with glycerol monolaurate as a bacteriostatic, toxin-inhibiting component. There is no mention of hydrophilic finishing of the fibers. DE 33 09 530 C1 describes sanitary absorbent towels, such as diapers or tampons, which are provided with a liquid-permeable covering film impregnated with a mixture of triglycerides and/or partial glycerides of $C_{8-18}$ coconut oil fatty acid as a skin-care component. However, the time taken by diapers with a liquid-permeable covering film according to the teaching of the German patent in question to absorb an aqueous sodium chloride solution at 20° C. increases by 50%.

The problem addressed by the present invention was to provide an improved process for hydrophilically finishing polyolefin- or polyester-containing fibers or nonwovens containing polyolefin or polyester fibers, the hydrophilic finish applied remaining intact, even after repeated wetting.

BRIEF SUMMARY OF THE INVENTION

It has now been found that these requirements are satisfied by a process in which the fibers or nonwovens are treated with a finish which contains monoesters of glycerol and certain fatty acids.

Accordingly, the present invention relates to a process for the hydrophilic finishing of fibers, which exclusively or predominantly contain polyolefins or polyesters, or of nonwovens which predominantly contain fibers such as these, characterized in that the nonwovens are treated with an aqueous dispersion of a finish which contains 75 to 100% by weight, based on the weight of the finish, of at least one monoester of glycerol and a fatty acid containing 6 to 14 carbon atoms and optionally up to 25% by weight of at least one alkyl glycoside corresponding to the general formula $RO(G)_x$, in which R is a primary linear or methyl-branched aliphatic radical containing 8 to 22 carbon atoms, G is a glycoside unit containing 5 or 6 carbon atoms and x is a number of 1 to 10.

DETAILED DESCRIPTION OF THE INVENTION

The process according to the invention is suitable for fibers which exclusively or predominantly, i.e. more than 50% by weight of which, contain polyolefins or polyesters, and for nonwovens which predominantly contain fibers such as these, fibers exclusively containing polyolefins or polyesters being preferred. Nonwovens of which 100% by weight consists of polyolefin or polyester fibers are particularly suitable. Polyolefin fibers are among the most commonly used fibers for the production of nonwovens. Examples of suitable polyolefins are polypropylene, polyethylene or copolymers of ethylene or propylene with butadiene. Polyester fibers, mainly polyethylene terephthalate fibers, are also used. Besides the fibers mentioned, other synthetic fibers suitable for the production of nonwovens may also be used, including for example fibers of Nylon®. Fibers consisting of two or more components, for example polyester/copolyester fibers or polypropylene/polyethylene fibers, are also particularly suitable.

The nonwovens used in the process according to the invention may be produced by any of the known processes for producing nonwovens which are described, for example, in Ullmann's Encyclopedia of Industrial Chemistry, Vol. A 17, VCH Weinheim 1994 pages 572–581. Nonwovens produced either by the dry laid process or by the spunbonded process are preferred. The dry laid process starts out from staple fibers which are normally separated by carding into individual fibers and are then laid together by an aerodynamic or hydrodynamic process to form the unbonded nonwoven. The unbonded nonwoven thus produced is then made up into the final nonwoven by a heat treatment known as thermobonding. To this end, the synthetic fibers are either heated to such an extent that their surface melts and the individual fibers are joined together at their points of contact or the fibers are coated with an additive which melts during the heat treatment, thus joining the individual fibers to one another. The bonds between the individual fibers are fixed by cooling. Besides this process, any of the other processes known for bonding nonwovens may of course also be used.

By contrast, the spunbonded process starts out from individual filaments which are formed by melt spinning from extruded polymers which are forced under high pressure through spinning jets. The filaments emerging from the spinning jets are bundled, stretched and laid to form a nonwoven which, normally, is then thermobonded.

The process according to the invention is particularly suitable for nonwovens produced by the spunbonded process or by the dry laid process.

In the process according to the invention, the fibers or nonwovens are treated with a finish which contains at least one monoester of glycerol and a $C_{6-14}$ fatty acid or a mixture consisting of at least one monoester of glycerol and a $C_{6-14}$ fatty acid and at least one alkyl glycoside. In the process according to the invention, the finish is applied to the untreated nonwoven in the form of an aqueous dispersion preferably containing from 5 to 30% by weight of the finish, based on the total weight of the dispersion. Any of the methods and machines typically used in the textiles industry, for example a padding machine, may be used for this purpose. The nonwoven is first contacted with the aqueous dispersion in a bath and the nonwoven thus treated is passed between two rollers, the water being squeezed out by the pressure of the rollers. The process according to the invention is preferably designed in such a way that the fibers or nonwovens receive an add-on of finish in a quantity of 0.3 to 2.0% by weight, based on the weight of the fibers or nonwovens.

The finish used in the process according to the invention contains at least one monoester of glycerol and a $C_{6-14}$ fatty acid. The monoglyceride makes up at least 75% of the total weight of the finish. The fatty acid glycerides should be of high purity, i.e. the percentage content of di- or triesters of glycerol and fatty acid should be small. Mixtures of various monoglycerides may also be used. Suitable fatty acids are, for example, caproic, caprylic, capric, lauric and myristic acid. A preferred ester is the monoester of glycerol and lauric acid, glycerol monolaurate.

The finish used in the process according to the invention may contain alkyl glycosides corresponding to the general formula $RO(G)_x$, where R is a primary linear or methyl-branched, more particularly 2-methyl-branched, aliphatic radical containing 8 to 22 and preferably 12 to 18 carbon atoms and G is a glycoside unit containing 5 or 6 carbon atoms, preferably glucose, as an additional component in quantities of 5 to 25% by weight. The degree of oligomerization x, which represents the distribution of monoglycosides and oligoglycosides, is a number of 1 to 10 and preferably a number of 1.2 to 1.4. Finishes containing alkyl glycosides in quantities of 5 to 20% by weight are particularly preferred.

In addition to the compounds described above, other substances known in the textiles field, for example antistatic agents or lubricants, may also be used in the finish. They are normally used in quantities of up to 20% by weight, based on the total weight of the finish.

It can also be of advantage to carry out the process according to the invention by treating the nonwoven with a finish which, in addition to the components already described, also contains quaternary ester amine compounds corresponding to general formula (I):

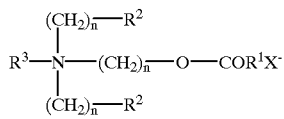

(I)

in which $COR^1$ is an aliphatic acyl group containing 12 to 22 carbon atoms and 0, 1, 2 or 3 double bonds, $R^2$ is H or OH and $R^3$ is an alkyl group containing 12 to 22 carbon atoms or preferably a group $(CH_2)_n$—O—$COR^1$, where n has a value of 1, 2 or 3 and X is either a halide, methosulfate, metho-phosphate or phosphate ion, in quantities of 5 to 25% by weight, based on the total quantity of finish.

In another embodiment, the invention relates to hydrophilic fibers exclusively or predominantly containing polyolefins or polyesters or to nonwovens predominantly containing such fibers which have been produced by the process according to the invention. The fibers or nonwovens show hydrophilic properties which preferably remain intact, even after repeated wetting. In particular, the nonwovens produced in accordance with the invention have liquid strike-through times of less than 10 seconds and, more particularly, less than 5 seconds. In the context of the present invention, liquid strike-through times are understood to be the times which a certain quantity of water or synthetic urine takes to pass through the nonwoven to an absorbent underlayer. This time is determined by EDANA Method No. 150.0-84 (EDANA=European Association of Nonwoven Manufacturers). For use in diapers or similar sanitary articles, the liquid strike-through time should be as short as possible in order to guarantee rapid transport of the liquid through the nonwoven to the absorbent material. In this way, the surface of the nonwoven remains dry and thus leads to increased wearing comfort. The nonwovens produced in accordance with the invention retain this favourable property, even after repeated use, and are further distinguished by the fact that, when the liquid strike-through time is determined preferably three times and more preferably five times in succession by EDANA Method No. 150.0-8, they always have a liquid strike-through time of less than 10 seconds and, more particularly, less than 5 seconds.

EXAMPLES

To determine the hydrophilicity of the variously produced nonwovens, the strike-through times of the test nonwovens were measured by EDANA Method No. 150.0-84. The measurements were carried out using a test instrument with a timer (Lister Tester from Lenzing AG). The test nonwovens (polypropylene spunbonded nonwoven weighing 20 g/m²—Lutrasil® 4420 from Freudenberg) were sprayed with an aqueous dispersion of the finish. The test nonwovens were then dried for one hour at 70° C.

For the actual measurements, 6 layers of a filter paper (Evans-Adlard FF3 WIS 150) were placed beneath one layer of the finished test nonwoven and then contacted with 5 ml of synthetic urine (1000 ml of dist. $H_2O$, 9 g NaCl) from the Lister Tester. The measurements were carried out at 20° C/65% relative air humidity. The time which the liquid takes to penetrate through the nonwoven was read off in seconds from the timer. In order to measure the hydrophilic properties of the nonwovens after repeated stressing, the test nonwoven was placed on a new layer of filter paper after the first measurement without being dried and the measurement was repeated. Times of at most 5 seconds after 5 repetitions were regarded as good. Times of more than 5 seconds were not reproduced.

The results are set out in Table 1 which shows the strike-through times in seconds for nonwovens treated with various finishes (average values of 5 measurements). The nonwovens were coated with 1.0 and 2.0% by weight, based on their weight, of the corresponding finish.

Nonwovens treated with the following finishes were tested. The figures in % by weight are based on the total weight of the finish. The respective finishes were used in the form of an aqueous dispersion containing 20% by weight of active substance, based on the aqueous dispersion.

Finish 1
100% by weight glycerol monolaurate
Finish 2
80% by weight glycerol monolaurate
15% by weight $C_{8-14}$ alkyl polyglucoside
Finish 3
80% by weight glycerol monolaurate
20% by weight $C_{8-14}$ alkyl polyglucoside The following finishes were used for comparison:
Finish C1
100% by weight $C_{8-14}$ alkyl polyglucoside
Table 1
Number of measurements

| Finish | 1 | 2 | 3 | 4 | 5 | 6 |
|---|---|---|---|---|---|---|
| 1 (Add-on 1.0%) | 3.12 | 3.98 | 4.40* | 5.00* | — | — |
| 1 (Add-on 2.0%) | 3.10 | 3.34 | 3.85 | 4.40 | 4.14 | 3.94 |
| 2 (Add-on 1.0%) | 2.81 | 3.11 | 4.07 | 4.83* | — | — |
| 2 (Add-on 2.0%) | 3.02 | 3.07 | 3.03 | 3.34 | 4.35 | 3.92 |
| 3 (Add-on 1.0%) | 3.02 | 3.02 | 3.88 | 4.83 | — | — |
| 3 (Add-on 2.0%) | 3.05 | 3.01 | 2.79 | 2.90 | 3.39 | 3.40 |
| C1 (Add-on 1.0%) | 3.30 | — | — | — | — | — |

*Average value of four measurements

It can be seen that a nonwoven produced in accordance with the invention treated with finish 1 still produces liquid strike-through times of at most 5 seconds at the fourth measurement both with an add-on of 2.0% and with an add-on of 1.0%. This effect is also obtained with the combination of glycerol monolaurate with an alkyl glucoside, as the nonwoven treated with finishes 2 and 3 shows. Finish 3 shows the best permanence. A nonwoven treated solely with an alkyl polyglucoside, i.e. with finish C1, also shows favourable hydrophilic properties. However, it does not retain these properties in the event of repeated stressing, so that the liquid strike-through times become much longer in the following measurements.

What is claimed is:

1. A process for hydrophilically finishing synthetic fibers or nonwoven substrates containing synthetic fibers comprising applying an effective amount of an aqueous finish composition onto the fibers or nonwoven substrates, the finish composition containing from 75 to 100% by weight, based on the weight of the composition, of at least one monoester of glycerol and a fatty acid having from 6 to 14 carbon atoms.

2. The process of claim 1 wherein the finish composition further contains up to 25% by weight, based on the weight of the composition, of an alkyl glycoside corresponding to formula I:

$$RO(G)_x \quad (I)$$

Wherein R is a primary linear or methyl-branched aliphatic radical having from 8 to 22 carbon atoms, G is a glycoside unit containing 5 or 6 carbon atoms, and x is a number from 1 to 10.

3. The process of claim 2 wherein in formula I, R is a 2-methyl branched aliphatic radical having from 12 to 18 carbon atoms, and x is a number from 1.2 to 1.4.

4. The process of claim 2 wherein the alkyl glcyoside is present in the composition in an amount of from 5 to 20% by weight, based on the weight of the composition.

5. The process of claim 1 wherein the monoester is glycerol monolaurate.

6. The process of claim 1 wherein the finish composition is applied onto the fibers or nonwoven substrates in the form of an aqueous dispersion containing from 5 to 30% by weight of the finish composition, based on the total weight of the aqueous dispersion..

7. The process of claim 1 wherein the synthetic fibers are selected from the group consisting of polyolefins, polyesters and mixtures thereof.

8. The process of claim 1 further comprising subsequently applying an additional 0.3 to 1.5% by weight, based on the weight of the fibers or nonwoven substrates, of the finish composition onto the fibers or nonwoven substrates.

9. The process of claim 1 wherein the hydrophilically finished fibers or nonwoven substrates have a liquid strike-through time of less than 10 seconds, as measured by EDANA Method No. 150.0-8.

10. The process of claim 9 wherein the hydrophilically finished fibers or nonwoven substrates have an average liquid strike-through time of less than 10 seconds, as measured by EDANA Method No. 150.0-8, after three successive measurements.

11. The product of the process of claim 1.

12. The product of the process of claim 2.

13. The product of the process of claim 3.

14. The product of the process of claim 4.

15. The product of the process of claim 5.

16. The product of the process of claim 6.

17. The product of the process of claim 7.

18. The product of the process of claim 8.

19. The product of the process of claim 9.

20. The product of the process of claim 10.

* * * * *